US009469849B2

(12) United States Patent
Ruegg

(10) Patent No.: US 9,469,849 B2
(45) Date of Patent: Oct. 18, 2016

(54) METHODS AND SYSTEMS FOR PURIFYING NON-COMPLEXED BOTULINUM NEUROTOXIN

(71) Applicant: Revance Therapeutics, Inc., Newark, CA (US)

(72) Inventor: Curtis L. Ruegg, Redwood City, CA (US)

(73) Assignee: Revance Therapeutics, Inc., Newark, CA (US)

( * ) Notice: Subject to any disclaimer, the term of this patent is extended or adjusted under 35 U.S.C. 154(b) by 0 days.

(21) Appl. No.: 14/796,235

(22) Filed: Jul. 10, 2015

(65) Prior Publication Data

US 2015/0322419 A1    Nov. 12, 2015

Related U.S. Application Data

(62) Division of application No. 13/394,506, filed as application No. PCT/US2010/053389 on Oct. 20, 2010, now abandoned.

(60) Provisional application No. 61/253,810, filed on Oct. 21, 2009.

(51) Int. Cl.
| | | |
|---|---|---|
| *C12N 15/10* | (2006.01) | |
| *C12N 1/08* | (2006.01) | |
| *C07K 1/18* | (2006.01) | |
| *C12N 9/52* | (2006.01) | |

(52) U.S. Cl.
CPC ......... *C12N 9/52* (2013.01); *C12Y 304/24069* (2013.01)

(58) Field of Classification Search
CPC ........ C12N 15/10; C12N 1/08; G01N 30/02; G01N 30/00; G01N 30/463; G01N 30/461; G01N 30/466
USPC .................. 436/518, 531; 530/412, 417, 344
See application file for complete search history.

(56) References Cited

U.S. PATENT DOCUMENTS

| | | |
|---|---|---|
| 3,184,394 A | 5/1965 | Schmidtberger et al. |
| 5,512,547 A | 4/1996 | Johnson et al. |

(Continued)

FOREIGN PATENT DOCUMENTS

| | | |
|---|---|---|
| JP | 2003-505343 | 2/2003 |
| JP | 2008-531046 | 8/2008 |

(Continued)

OTHER PUBLICATIONS

Dux, Michael P. et al., "Purification and scale-up of a recombinant heavy chain fragment C of botulinum neurotoxin serotype E in *Pichia pastoris* GS115", Protein Expression and Purification, 45 (2006) pp. 359-367.

(Continued)

*Primary Examiner* — Albert Navarro
*Assistant Examiner* — Ginny Portner
(74) *Attorney, Agent, or Firm* — Kenneth H. Sonnenfeld; King & Spalding LLP

(57) ABSTRACT

Methods and systems for chromatographically purifying a *botulinum* neurotoxin are provided. These methods and systems allow for efficient purification of a non-complexed form of the *botulinum* neurotoxin in high purity and yield that can be used as an active ingredient in pharmaceutical preparations.

67 Claims, 1 Drawing Sheet

(56) References Cited

U.S. PATENT DOCUMENTS

| | | | |
|---|---|---|---|
| 6,818,409 | B2 | 11/2004 | Oguma |
| 6,994,859 | B1 | 2/2006 | Singh et al. |
| 7,193,066 | B1 | 3/2007 | Chaddock et al. |
| 7,211,261 | B1 * | 5/2007 | Moyer .................. A61K 8/64 424/234.1 |
| 7,214,787 | B1 | 5/2007 | Smith et al. |
| 7,354,740 | B2 | 4/2008 | Xiang et al. |
| 7,452,697 | B2 | 11/2008 | Luo et al. |
| 7,927,836 | B2 * | 4/2011 | Doelle ................ C12M 37/02 435/286.5 |
| 7,964,199 | B1 * | 6/2011 | Bigalke ............ C07K 16/1282 424/184.1 |
| 8,129,139 | B2 | 3/2012 | Ton et al. |
| 8,324,349 | B2 | 12/2012 | Ton et al. |
| 8,357,541 | B2 * | 1/2013 | Ton .................... C07K 14/33 436/161 |
| 8,398,998 | B2 * | 3/2013 | Bigalke ............ A61K 38/4893 424/234.1 |
| 8,409,828 | B2 | 4/2013 | Xiang et al. |
| 8,927,229 | B2 * | 1/2015 | Ton .................... C07K 14/33 435/41 |
| 8,932,827 | B2 * | 1/2015 | Ton .................... C07K 14/33 435/41 |
| 9,206,409 | B2 * | 12/2015 | Ton .................... C07K 14/33 |
| 2003/0008367 | A1 | 1/2003 | Oguma |
| 2004/0259197 | A1 | 12/2004 | Suppmann et al. |
| 2005/0238669 | A1 | 10/2005 | Xiang et al. |
| 2006/0228780 | A1 | 10/2006 | Luo et al. |
| 2007/0026019 | A1 * | 2/2007 | Hunt .................. A61K 9/0019 424/239.1 |
| 2007/0037257 | A1 | 2/2007 | Smith et al. |
| 2007/0154880 | A1 | 7/2007 | Ella et al. |
| 2009/0123497 | A1 | 5/2009 | Luo et al. |
| 2009/0124790 | A1 | 5/2009 | Luo et al. |
| 2011/0008843 | A1 | 1/2011 | Ton et al. |
| 2011/0171226 | A1 | 7/2011 | Johnson et al. |
| 2011/0206729 | A1 | 8/2011 | Akiyoshi et al. |
| 2012/0245324 | A1 | 9/2012 | Ton et al. |
| 2013/0171716 | A1 | 7/2013 | Xiang et al. |

FOREIGN PATENT DOCUMENTS

| | | | | |
|---|---|---|---|---|
| JP | 2011-074025 | * | 4/2011 | ............ C07K 14/33 |
| KR | 10-2005-0074806 | * | 7/2005 | ............... C12P 1/04 |
| WO | 00/74703 | * | 12/2000 | ............ A61K 38/16 |
| WO | 2004/108750 | * | 12/2004 | ............... C07K 1/14 |
| WO | 2006/133818 | * | 12/2006 | ............. C12M 1/00 |

OTHER PUBLICATIONS

DasGupta, B. R. et al., "Purification and amino acid composition of type A botulinum neurotoxin", Toxicon, vol. 22, Issue 3, (1984), pp. 415-424.

Simpson, Lance L. et al., "Isolation and Characterization of the Botulinum Neurotoxins", Academic Press, Inc., Methods in Enzymology, vol. 165, (1988), pp. 76-85.

Gessler, Frank, "A new scaleable method for the purification of botulinum neurotoxin type E", Journal of Biotechnology 119 (2005) pp. 204-211.

Gessler, Frank and Bohnel, H., "Production and Purification of Clostridium botulinum type C and D Neurotoxin," FEMS Immunol. And Medical Microbiology, 25 (1999), pp. 361-367.

Prabakaran, S. et al., "Botulinum neurotoxin types B and E: purification, limited proteolysis by endoproteinase Glu-C and pepsin, and comparison of their identified cleaved sites relative to the three-dimensional structure of type A neurotoxin", Toxicon 39 (2001) pp. 1515-1531.

The International Search Report and Written Opinion from related PCT Application No. PCT/US2010/053389, mailed Dec. 17, 2010, 6 sheets.

Revance Therapeutics, Inc., Extended European Search Report for related EP Patent Application No. 10825598.5, issued by the European Patent Office Oct. 10, 2013, 14 pages.

Revance Therapeutics, Inc., Notification of the Second Office Action for related CN Patent Application No. 201080045567.0, issued by the State Intellectual Property Office, PRC, Jan. 8, 2014, 9 pages.

Revance Therapeutics, Inc., English translation of Notifications of Reasons for Refusal, issued in related Japanese Patent Application No. 2012-535338, Nov. 17, 2014, 6 pages.

* cited by examiner

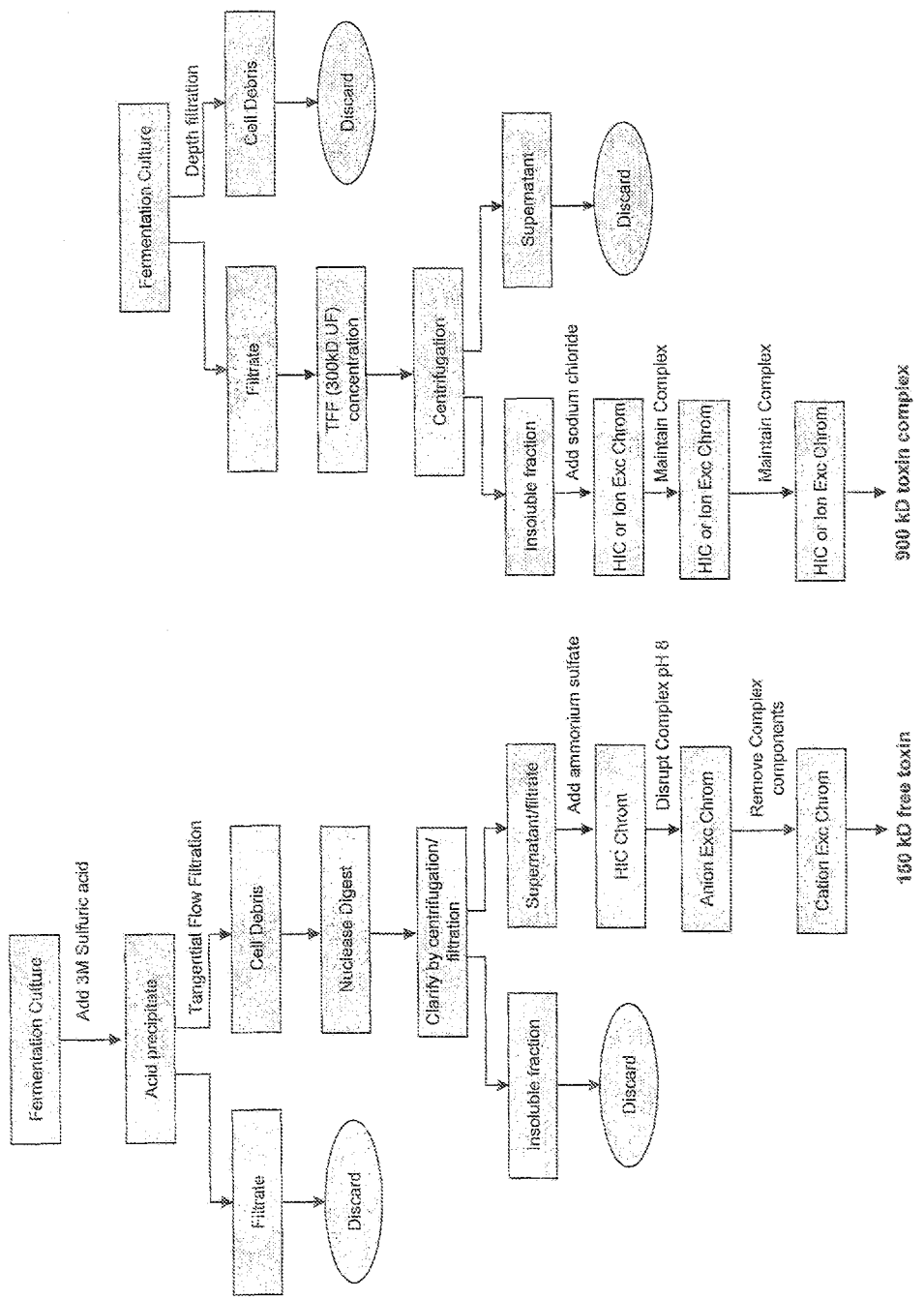

METHODS AND SYSTEMS FOR PURIFYING NON-COMPLEXED BOTULINUM NEUROTOXIN

CROSS-REFERENCE TO RELATED APPLICATIONS

This application is a divisional of U.S. patent application Ser. No. 13/394,506, filed on Mar. 19, 2012, which is a 35 U.S.C. §371 National Stage Entry of International PCT Application Number PCT/US2010/053389, filed on Oct. 20, 2010, which claims benefit of priority to U.S. Provisional Patent Application No. 61/253,810, filed on Oct. 21, 2009. The entire contents of these applications are hereby incorporated herein by reference.

FIELD OF THE INVENTION

This invention relates generally to chromatographic methods and systems for purifying free *botulinum* neurotoxin from cell cultures to produce a high purity, high potency product.

BACKGROUND OF THE INVENTION

*Botulinum* toxin is a neurotoxic protein produced by the bacterium *Clostridium botulinum*, as well as other *Clostridial* species, such as *Clostridium butyricum*, and *Clostridium baraffi*. The toxin blocks neuromuscular transmission and causes a neuro-paralytic illness in humans and animals, known as botulism. *C. botulinum* and its spores commonly occur in soil and putrefying animal carcasses, and can grow in improperly sterilized or improperly sealed food containers, which are the cause of many botulism cases. Botulism symptoms can include difficulty walking, swallowing, and speaking, and can progress to paralysis of the respiratory muscles and finally death.

*Botulinum* toxin type A is the most lethal natural substance known to man. In addition to serotype A, six other generally immunologically distinct *botulinum* toxins have been characterized, namely *botulinum* toxin serotypes B, $C_1$, D, E, F, and G. The different serotypes can be distinguished by neutralization with type-specific antibodies and vary in severity of paralysis they evoke and the animal species they mostly affect. The molecular weight of the *botulinum* toxin protein molecule, for each of the known *botulinum* toxin serotypes, is about 150 kD, composed of an about 100 kD heavy chain joined to an about 50 kD light chain. Nonetheless, the *botulinum* toxins are released by *Clostridial* bacteria as complexes of the 150 kD toxin with one or more non-toxin proteins. For example, *botulinum* toxin type A exists as 900 kD, 500 kD and 300 kD complexes (approximate molecular weights).

Despite the known toxic effects, *Botulinum* toxin type A is clinically used to treat a variety of indications, including, e.g., neuromuscular disorders characterized by skeletal muscle hyperactivity. For example, BOTOX® is the trademark of a *botulinum* toxin type A complex available commercially from Allergan, Inc., of Irvine, Calif. *Botulinum* toxin type A finds use, for example, in the treatment of essential blepharospasm, strabismus, cervical dystonia, and glabellar line (facial) wrinkles Other serotypes also have been used clinically. A *botulinum* toxin type B, for example, has been indicated for use in treating cervical dystonia. The *botulinum* toxins are believed to bind with high affinity to the presynaptic membrane of motor neurons, translocate into the neuron, and thereafter block the presynaptic release of acetylcholine.

The *botulinum* toxin for clinical use is typically isolated from cell culture and various purification approaches have been used. Historically, the toxin is purified in complexed form by a series of precipitation and tangential flow filtration steps. See, e.g., Schantz E. J., et al., Properties and use of *botulinum* toxin and other microbial neurotoxins in medicine, Microbiol Rev 1992 March 56(1):80-99. Such approaches have provided relatively low yields, however, typically less than about 10%. Other approaches have used size exclusion, ion exchange, and/or affinity chromatography. See, e.g., Schmidt J. J., et al., Purification of type E *botulinum* neurotoxin by high-performance ion exchange chromatography, Anal. Biochem. 1986 July; 156(1):213-219; Simpson L. L., et al., Isolation and characterization of the *botulinum* neurotoxins, Harsman S, ed. Methods in Enzymology. Vol. 165, Microbial Toxins: Tools in Enzymology San Diego, Calif.: Academic Press; Vol. 165: pages 76-85 (1988); Kannan K., et al., Methods development for the biochemical assessment of Neurobloc (*botulinum* toxin type B), Mov Disord 2000; 15(Suppl 2):20 (2000); Wang Y. C., The preparation and quality of *botulinum* toxin type A for injection (BTXA) and its clinical use, Dermatol Las Faci Cosm Surg 2002; 58 (2002); and U.S. Pat. Appl. Publ. No. 2003/0008367.

Still other approaches have focused on just one of the toxin's heavy or light chains, rather than a complete and biologically active *botulinum* toxin protein. For example, one of the chains is individually synthesized by recombinant means. See, e.g., Zhou L., et al., Expression and purification of the light chain of *botulinum* neurotoxin A: A single mutation abolishes its cleavage of SNAP-25 and neurotoxicity after reconstitution with the heavy chain, Biochemistry 1995; 34(46):15175-81 (1995); and Johnson S. K., et al., Scale-up of the fermentation and purification of the recombination heavy chain fragment C of *botulinum* neurotoxin serotype F, expressed in *Pichia pastoris*, Protein Expr and Purif 2003; 32:1-9 (2003). These approaches, however, require extra steps to reform a complete and biologically active *botulinum* toxin protein.

A more recent approach involves the use of hydrophobic interaction chromatography, mixed mode, and/or ion exchange chromatography to purify a *botulinum* toxin as a complex. See, e.g., U.S. Pat. Nos. 7,452,697 and 7,354,740, which are hereby incorporated by reference.

Accordingly, there is a need in the art for improved purification methods for isolating complete *botulinum* toxin proteins in stable, biologically active, but non-complexed forms. It is therefore an object of the invention to provide compositions and methods addressing these and other needs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

This invention relates to systems and methods for purifying a non-complexed *botulinum* toxin. In one embodiment, the method comprises purifying crude non-complexed *botulinum* toxin to obtain a purified non-complexed *botulinum* toxin. In this embodiment, the method comprises loading an anion exchange column with the crude non-complexed *botulinum* toxin to capture the non-complexed *botulinum* toxin on the anion exchange column; eluting the non-complexed *botulinum* toxin with buffer to give an eluent comprising the non-complexed *botulinum* toxin; loading a cation exchange column with the eluent from the anion exchange to column to permit capture of the non-complexed *botulinum* toxin; and eluting the non-complexed *botulinum* toxin with another buffer to give an eluent, thereby obtaining a purified non-complexed *botulinum* toxin.

In certain embodiments, the *botulinum* toxin complex is itself obtained by a number of chromatography steps. In some embodiments, a method for obtaining the *botulinum* toxin complex comprises obtaining a sample comprising a *botulinum* toxin complex; loading a hydrophobic interaction column with the sample to permit capture of the toxin, wherein the captured *botulinum* toxin comprises a complexed *botulinum* toxin; and eluting the complexed *botulinum* toxin. The non-complexed *botulinum* toxin is then dissociated from the complex and the non-complexed *botulinum* toxin is purified according to the method described above. In some embodiments, the sample is obtained by subjecting a fermentation culture comprising *botulinum* toxin to acid to obtain an acid precipitate, which may be subjected to additional pre-chromatography purification steps, non-limiting examples of which include tangential flow filtration to concentrate the insoluble material of the precipitate, nuclease digest, clarifying centrifugation and/or filtration.

In some embodiments, the sample is subjected to a nuclease digestion before loading on the hydrophobic interaction column. Preferably, the nuclease is derived in an animal-product-free process, and even more preferably the entire purification process is animal product free or at least substantially animal product free.

In some embodiments, the sample to be used in the chromatographic separations is preferably a supernatant or filtrate fraction.

The purified non-complexed *botulinum* toxin comprises at least one of *botulinum* toxin type A, B, $C_1$, D, F, F and G, and preferably a *botulinum* toxin type A having a molecular weight of about 150 kD. In some preferred embodiments, the purified non-complexed *botulinum* toxin is at least 98% pure; and/or has an activity of at least 200 $LD_{50}$ units/ng. In some embodiments, the method produces a yield of at least about 2 mg/L fermentation culture. In other embodiments, the method produces a yield of about 1 to about 2 mg/L fermentation culture.

These and other aspects of the invention will be better understood by reference to the following detailed description of the invention.

BRIEF DESCRIPTION OF THE FIGURES

FIG. 1 is a summary flow chart comparing one embodiment of a process according to the instant invention for directly purifying a non-complexed *botulinum* toxin (FIG. 1A) with a process for purifying a complexed *botulinum* toxin (FIG. 1B).

DETAILED DESCRIPTION

This invention relates to systems and methods for purifying a non-complexed *botulinum* toxin. In certain embodiments, the method comprises purifying a crude non-complexed *botulinum* toxin by loading an anion exchange column with the crude non-complexed *botulinum* toxin to permit capture of the non-complexed *botulinum* toxin by the anion exchange column. Non-complexed *botulinum* toxin is then eluted with buffer to give an eluent comprising the non-complexed *botulinum* toxin. The eluent from the anion column is loaded on a cation exchange column to permit capture of the non-complexed *botulinum* toxin and the purified non-complexed *botulinum* toxin is eluted with buffer, thereby obtaining a purified non-complexed *botulinum* toxin.

In some embodiments, the invention provides for the purification of non-complexed *botulinum* toxin in a relatively small number of steps to produce a high yield, high purity, and high potency product. Processes and systems within the scope of the invention can be used to efficiently produce a stable but non-complexed *botulinum* toxin from fermentation cultures. In other embodiments, the method further comprises providing a sample comprising *botulinum* toxin complex and loading a hydrophobic interaction column with the sample so as to permit capture of the *botulinum* toxin complex by the hydrophobic interaction column. The *botulinum* toxin complex is then eluted from the column with buffer. Crude non-complexed *botulinum* toxin is dissociated from the *botulinum* toxin complex to obtain a mixture comprising the crude non-complexed *botulinum* toxin. In this embodiment, the mixture comprising crude non-complexed *botulinum* toxin is purified to obtain pure or substantially pure *botulinum* toxin according to the method described above.

One aspect of this invention is the recognition that a pharmaceutical composition comprising non-complexed *botulinum* toxin as an active ingredient can provide greater purity compared to one comprising a complexed form. Non-toxin proteins typically associated with a *botulinum* toxin complex can account for about 90% by weight of the complex. Thus, providing a *botulinum* toxin as a complex necessarily includes at least about 90% by weight of impurities. In other words, at least about 80 to about 90% by weight of the pharmaceutical composition will include cell-derived impurities that are not part of the active molecule nor necessary for its biological activity. Such impurities, however, represent cell-derived materials that when administered to a patient may increase the risk of unwanted immunological reactions to the drug; may increase the risk of unwanted side effects; and/or may increase the risk of transmission of pathogenic agents. In contrast, the high purity of a non-complexed product, obtainable by methods and systems described herein, reduces the amount of host cell impurities that may remain in the pharmaceutical composition, thereby reducing the attendant risks of unwanted reactions and/or transmission. Accordingly, processes and systems described herein can provide a *botulinum* toxin in a form more readily suited to the preparation of safer, purer pharmaceutical compositions.

Moreover, unlike complexed forms, free *botulinum* toxin prepared in accordance with the method described herein does not need to be stabilized for storage in blood-derived products. *Botulinum* toxin type A complex, for example, is typically stabilized in an excipient comprising albumin, which is derived from human blood. For example, BOTOX® consists of a purified *botulinum* toxin type A complex, human serum albumin, and sodium chloride packaged in vacuum-dried form. The same is true for Dysport and Xeomin. While screenings reduce likelihood of contamination with pathogenic agents, use of human blood in pharmaceutical preparations generally increases the risk of unwanted transmission of certain pathogenic agents, e.g., agents which are not or cannot yet be screened out. In contrast, free *botulinum* toxin prepared according to the instant invention can be stably stored, as taught herein, in ammonium sulfate. Further, in some preferred embodiments, methods and systems of the instant invention are substantially, essentially, or entirely animal product free, as discussed herein. The ability to also stably store the toxin product substantially, essentially, or entirely animal-product free, further reduces potential risks associated with animal-derived products. Accordingly, processes and systems described herein provide a *botulinum* toxin in a form particularly suited to pharmaceutical applications in terms of safety, e.g., where the pharmaceutical composition may be prepared and stored substantially, essentially, or entirely animal-product free.

In certain preferred embodiments, the processes and systems described herein are scalable and/or cGMP compliant. Accordingly, methods and systems described herein may be used on a commercial, industrial scale, to produce non-complexed *botulinum* toxin for use, e.g., in pharmaceutical compositions. A cGMP compliant process or system refers to one that can comply with the regulatory requirements for current good manufacturing practices, as required by the U.S. Code of Federal Regulations. In some preferred embodiments, the non-complexed *botulinum* toxin product is particularly suited to large scale production due to its ease of storage and usability, high activity, high purity, stability, and/or improved safety.

"*Botulinum* toxin" as used herein refers to a neurotoxin protein molecule that can be produced by a *Clostridial* bacterium, as well as recombinantly produced forms thereof. A recombinant *botulinum* toxin can have the light chain and/or heavy chain of the toxin protein synthesized via recombinant techniques, e.g., by a recombinant *Clostridial* and/or non-*Clostridial* species. "*Botulinum* toxin" is used interchangeably herein with the related expressions "*botulinum* neurotoxin," "neurotoxin" or simply "toxin." "*Botulinum* toxin" encompasses any of the *botulinum* toxin serotypes A, B, $C_1$, D, E, F and G, and also encompasses both complexed and non-complexed forms.

By "complexed form" is meant a *botulinum* toxin complex comprising a *botulinum* toxin protein (i.e., the toxin molecule with a molecular weight of about 150 kD) as well as at least one associated native non-toxin protein. Non-toxin proteins that make up the complexes typically include non-toxin hemagglutinin protein and non-toxin non-hemagglutinin protein. Thus complexed forms may comprise a *botulinum* toxin molecule (the neurotoxic component) and one or more non-toxin hemagglutinin proteins and/or one or more non-toxin non-hemagglutinin proteins. In certain embodiments, the molecular weight of the complex is greater than about 150 kD. For example, complexed forms of the *botulinum* toxin type A can have molecular weights of about 900 kD, about 500 kD or about 300 kD. Complexed forms of *botulinum* toxin types B and $C_1$ can have a molecular weight of 500 kD. Complexed forms of *botulinum* toxin type D can have a molecular weight of about 300 kD or about 500 kD. Finally, complexed forms of *botulinum* toxin types E and F can have a molecular weight of about 300 kD.

"Non-complexed" *botulinum* toxin refers to an isolated, or essentially or substantially isolated, *botulinum* toxin protein having a molecular weight of about 150 kD. That is, "non-complexed" forms exclude non-toxin proteins, such as non-toxin hemagglutinin and non-toxin non-hemagglutinin proteins, normally associated with the complexed form. "Non-complexed" *botulinum* toxin is used interchangeably herein with "free" *botulinum* toxin. All the *botulinum* toxin serotypes made by native *Clostridium botulinum* bacteria are synthesized by the bacteria as inactive single chain proteins which are then cleaved or nicked by proteases to become neuroactive. The protein comprises an about 100 kD heavy chain joined by a disulfide bond to an about 50 kD light chain.

*Botulinum* toxin complexes can be dissociated into toxin and non-toxin proteins by various means, including, for example, raising the pH to about 7.0, treating the complex with red blood cells at a pH of about 7.3, and/or subjecting the complex to a separation process, such as column chromatography in a suitable buffer at a pH of about 7 to about 8.

The instant invention encompasses systems and methods that enable purification of a non-complexed *botulinum* toxin, without associated non-toxin proteins conventionally believed necessary during the purification process to maintain stability. In preferred embodiments, the methods and systems described herein facilitate purification of the free *botulinum* toxin without loss of stability. By "stability" or "stable" is meant that the *botulinum* toxin protein molecule retains both the about 100 kD heavy chain and the about 50 kD light chain, joined to each other by a disulfide bond, and in a conformation that allows for biological activity.

In some embodiments, a particular system within the scope of the present invention is operated in conjunction with a particular method within the scope of the present invention. A system within the scope of the present invention can comprise a plurality (preferably consecutive series) of chromatography columns for use with a corresponding plurality (preferably consecutive series) of chromatography steps. Further, a system within the scope of the instant invention may comprise a plurality (preferably a consecutive series) of non-chromatography devices, such as filtration and/or centrifugation apparatus, for use with a corresponding plurality (preferably consecutive series) of non-chromatography steps, e.g., as pre-chromatography steps.

In preferred embodiments, a process within the scope of the present invention comprises obtaining a sample comprising *botulinum* toxin from a fermentation culture; subjecting it to a number of pre-chromatography purifications; and then passing it through a plurality of chromatography columns to obtain a highly purified, highly potent non-complexed *botulinum* toxin. Such a purified free *botulinum* toxin finds use in the preparation of pharmaceutical compositions comprising the free *botulinum* toxin as an active ingredient.

The overall steps for both pre-chromatography and chromatography processes for some preferred embodiments of the instant invention are illustrated in FIG. 1A. For comparison, FIG. 1B shows a conventional method for obtaining purified *botulinum* toxin complex. Briefly, FIG. 1B depicts a process involving depth filtration of a fermentation culture, followed by tangential flow filtration of the filtrate obtained (using 300 kD ultramicrofiltration); followed by a clarifying centrifugation step. The pellet (insoluble fraction) resulting from the centrifugation step is then re-suspended in sodium chloride, and loaded onto a hydrophobic interaction or ion exchange column. The chromatographic purification step is repeated at least three times to give a final eluent containing the 900 kD *botulinum* toxin type A complex.

Fermentation and Acid Precipitation

As FIG. 1A illustrates, the non-complexed *botulinum* toxin is generally purified from a fermentation culture. A "fermentation culture" as used herein refers to a culture or medium comprising cells, and/or components thereof, that are synthesizing and/or have synthesized at least one *botulinum* toxin. For example, *Clostridial* bacteria, such as

*Clostridium botulinum*, may be cultured on agar plates in an environment conducive to bacterial growth, such as in a warm anaerobic atmosphere. The culture step typically allows *Clostridial* colonies with desirable morphology and other characteristics to be obtained. Selected cultured *Clostridial* colonies then can be fermented in a suitable medium as a fermentation culture. The cultured cells may include non-*Clostridial* species as the host cells, such as *E. coli* or yeast cells, that are rendered capable of biosynthesizing a *botulinum* toxin by recombinant technology. Suitable fermentation culture conditions can depend on the host cells used and are generally known in the art.

In preferred embodiments, fermentation may be allowed to progress to completion, such that cells are mature and have biosynthesized a *botulinum* toxin. Growth of *Clostridium botulinum* cultures is usually complete after about 24 to about 36 hours. After a certain additional period of time, the bacteria typically lyse and release into the medium the synthesized *botulinum* toxin complex in a complexed form. For example, during a fermentation of about 60 to about 96 hours, most *Clostridium botulinum* cells undergo lysis and release *botulinum* toxin type A complex.

In some embodiments, the fermentation culture can comprise one or more animal products, such as animal proteins, used in conventional fermentation culture procedures. For example, *botulinum* toxin can be produced by anaerobic fermentation of *Clostridium botulinum* using a modified version of the well known Schantz process (see e.g. Schantz E. J., et al., Properties and use of *botulinum* toxin and other microbial neurotoxins in medicine, Microbiol Rev 1992 March; 56(1):80-99; Schantz E. J., et al., Preparation and characterization of *botulinum* toxin type A for human treatment, chapter 3 in Jankovic J, ed. Neurological Disease and Therapy. Therapy with *botulinum* toxin (1994), New York, Marcel Dekker; 1994, pages 41-49, and; Schantz E. J., et al., Use of crystalline type A *botulinum* toxin in medical research, in: Lewis G E Jr, ed. Biomedical Aspects of Botulism (1981) New York, Academic Press, pages 143-50, each incorporated herein by reference). Both the Schantz and the modified Schantz process for obtaining a *botulinum* toxin make use of animal products, including animal-derived-Bacto-Cooked Meat medium in the culture vial, and casein in the fermentation media. Additionally, the Schantz toxin purification makes use of DNase and RNase from bovine sources to hydrolyze nucleic acids present in the fermentation culture.

However, administration of a pharmaceutical containing an active ingredient that was purified using a process involving animal-derived products can subject a patient to a potential risk of receiving various pathogenic agents. For example, prions may be present in a pharmaceutical composition comprising contaminating animal-derived products, such as the prion responsible for Creutzfeldt-Jacob disease. As another example, there is a risk of transmitting a spongiform encephalopathy (TSE), such as a bovine spongiform encephalopathy (BSE) when animal products are used in the process of making a pharmaceutical composition. The use of a *botulinum* toxin obtained via processes free of animal products, however, reduces such risks. Therefore, in some preferred embodiments, the invention provides a process that is free of animal products, or essentially or substantially animal-product-free (APF). "Animal product free", "essentially animal product free", or "substantially animal product free" encompasses, respectively, "animal protein free", "essentially animal protein free", or "substantially animal protein free" and respectively means the absence, essential absence, or substantial absence, of products derived from animals, non-limiting examples of which include products derived from blood or pooled blood. "Animal" is used herein to refer to a mammal (such as a human), bird, reptile, amphibian, fish, insect, spider or other animal species, but excludes microorganisms, such as bacteria and yeasts.

An animal-product-free process (or a substantially or essentially animal product-free-process) refers to a process that is entirely, substantially, or essentially free of animal-derived products, reagents and proteins, such as immunoglobulins, other blood products, by-products, or digests; meat products, meat by-products, meat digests; and milk or dairy products, by-products or digests. Accordingly, an example of an animal-product free fermentation culture procedure is a fermentation process, such as bacterial culturing, which excludes blood, meat, and dairy products, by-products, and digests. An animal-product-free fermentation process for obtaining a non-complexed *botulinum* toxin reduces the possibility of contamination with viruses, prions or other undesirable agents, which can then accompany the toxin when administered to humans.

Animal-product-free fermentation procedures using *Clostridium* cultures are described, e.g., in U.S. Pat. Nos. 7,452,697 and 7,354,740, hereby incorporated by reference. For example, the growth media for production of the *botulinum* toxin may comprise vegetable-based products, instead of animal-derived products, such as soy-based products and/or the debittered seed of *Lupinus campestris*. Soy-based fermentation media for use in an animal product free fermentation culture, for example, can comprise a soy-based product, a source of carbon such as glucose, salts such as NaCl and KCl, phosphate-containing ingredients such as $Na_2HPO_4$ and $KH_2PO_4$, divalent cations such as iron and magnesium, iron powder, amino acids such as L-cysteine and L-tyrosine, and the like. Preferably, the soy is hydrolyzed soy and the hydrolyzation has been conducted using enzymes not derived from animals. Sources of hydrolyzed soy include but are not limited to Hy-Soy (Quest International), Soy peptone (Gibco) Bac-soytone (Difco), AMISOY (Quest), NZ soy (Quest), NZ soy BL4, NZ soy BL7, SE50M (DMV International Nutritionals, Fraser, N.Y.), and SE50MK (DMV).

As FIG. 1A illustrates, in certain embodiments a sample comprising *botulinum* toxin is obtained from a fermentation culture. For example, after a certain period of fermentation, in either animal product free or non-animal product free media, *botulinum* toxin complex is released into the medium and can be harvested by precipitation. For example, in some embodiments, as in the well-known Schantz process, the fermentation medium comprising the *botulinum* toxin may be subjected to acid precipitation to encourage the *botulinum* toxin complexes to associate with cell debris and form an acid precipitate. In some particularly preferred embodiments, about 3 M sulfuric acid solution may be added to the fermentation culture to form the acid precipitate. Preferably, the pH is reduced to about 3 to about 4, more preferably to about 3.2 to about 3.8, and even more preferably about 3.5. In some embodiments, the culture temperature is also reduced, e.g., to about below 25° C., 24° C., 23° C., 22° C., 21° C., or 20° C. These conditions further enhance the association of *botulinum* toxin complexes with cell debris. The acid precipitate formed will comprise bound *botulinum* toxin complexes and can be used as the starting material in further purification steps, such as clarification steps; whereas the filtrate is discarded.

In contrast, the conventional process depicted in FIG. 1B does not include an acid precipitation step. That is, while the purification procedure also begins with a fermentation culture comprising a *botulinum* toxin complex, the culture medium is subjected to depth filtration, and the filtrate, rather than the cell debris, is used in subsequent purification steps. In the FIG. 1B process, the cell debris is discarded, rather than the filtrate, whereas, as illustrated in FIG. 1A, the filtrate is discarded and the cell debris (acid precipitate) is used for further purification steps, e.g., in the pre-chromatography purifications discussed below.

Pre-Chromatography Purifications

In some embodiments, the sample obtained from the fermentation medium is subjected to one or more pre-chromatography purifications. Pre-chromatography purifications can include at least one of tangential flow filtration, nuclease digest, and clarifying centrifugation and/or filtration. A non-limiting example of a process flow containing pre-chromatography purification contemplated by the invention is provided in FIG. 1A. As noted above, in preferred embodiments, the pre-chromatography procedures are carried out on a precipitate (or insoluble fraction) of a fermentation culture comprising the *botulinum* toxin, rather than on the fermentation culture itself or on a filtrate derived therefrom, as in the process illustrated in FIG. 1B. That is, in preferred embodiments of the invention, pre-chromatography (clarification) steps start with the acid precipitate (insoluble fraction).

In some embodiments, the sample (acid precipitate or insoluble fraction) comprising a *botulinum* toxin is subjected to tangential flow filtration. Tangential flow filtration is a process typically used to clarify, concentrate, and/or purify proteins. In contrast to normal flow filtration, where fluid moves directly towards a filter membrane under applied pressure, in tangential flow filtration, the fluid moves tangentially along, or parallel to, the surface of the membrane. Applied pressure serves to force a portion of the fluid through the filter membrane, to the filtrate side, while particulates and macromolecules too large to pass through membrane pores are retained. Unlike normal flow filtration, however, the retained components do not build up at the membrane surface but are swept along by the tangentially flowing fluid. In certain preferred embodiments, tangential flow filtration is used to concentrate the insoluble material (cell debris) with which the *botulinum* complex is associated, while permitting filtrate to pass through the membrane pores. (See, e.g., FIG. 1A.) Tangential flow filtration parameters, such as pore size, feed flow, applied pressure, and the like, may be selected by those of skill in the art to concentrate cell debris and to produce a more concentrated sample comprising the *botulinum* toxin complex. In some particularly preferred embodiments, for example, tangential flow filtration with filters having a pore size of about 0.1 μm may be used.

In some embodiments, the sample comprising a *botulinum* toxin is subjected to nuclease digestion. Nuclease digestion can facilitate removal of nucleic acid components with which the *Botulinum* toxin complexes tend to associate. In certain preferred embodiments, nuclease digestion follows tangential flow filtration and is carried out on the concentrated cell debris obtained therefrom. (See, e.g., FIG. 1A.) For example, the concentrated cell debris sample may have its pH adjusted to allow nuclease activity and may be incubated with one or more suitable nucleases, such as DNases and/or RNases that digest (hydrolyze) DNA and/or RNA, respectively. Depending on the nuclease enzyme used, suitable pH may be about 5 to about 7, preferably about 6. In some embodiments, benzamidine is used as a protease inhibitor to prevent proteolysis of the toxin during nuclease digestion step. The nuclease used may be derived from any suitable source, including animal sources and/or non-animal sources.

In more preferred embodiments, the nuclease is obtained from a non-animal source, to provide an animal-product-free nuclease and an animal-product-free process. Accordingly, the instant invention encompasses animal-product-free processes and systems (or substantially or essentially animal product free processes and systems) for purifying *botulinum* toxin which comprise use of a nuclease. An animal-product-free nuclease may be made recombinantly, e.g., using recombinant bacteria, yeasts, or other suitable microorganisms, which have been transformed to express a DNase and/or RNase for use in a nuclease digestion step according to processes described herein. Nuclease digestion typically reduces the nucleic acid content of the sample, as the host cell nucleic acids are degraded and their removal is facilitated. For example, hydrolyzed nucleic acids and other low molecular weight impurities can be removed by further purification steps.

In certain embodiments, the sample comprising a *botulinum* toxin may be subjected to clarifying centrifugation and/or filtration. Clarifying centrifugation or filtration refers to centrifugation or filtration steps used to remove gross elements, such as whole and lysed cells and cell debris, from the sample, resulting in a measurably clearer sample. In certain embodiments, the centrifugation is performed at about 10,000×g to about 30,000×g, more preferably at about 15,000×g to about 20,000×g, and most preferably at about 17,700×g. Clarifying filtration will typically comprise normal flow filtration, also called "dead end" filtration, where fluid is moved directly toward a filter media under applied pressure, and particulates too large to pass through the filter pores accumulate at the surface or within the media itself, while smaller molecules pass through as the filtrate. In some particularly preferred embodiments, the sample is mixed with ammonium sulfate and normal flow filtration is performed using a filter with a pore size of about 0.1 to about 0.3 μm, and more preferably a pore size of about 0.2 μm. (See, e.g., FIG. 1A.) In certain particularly preferred embodiments, one or more clarifying step(s) follow the nuclease digestion step. In certain still more preferred embodiments, one or more clarifying step(s) immediately precede purification by chromatography.

Notably, in preferred embodiments, the clarified supernatant or filtrate provides the *botulinum* toxin-containing sample for use in further purification steps, such as the chromatography purification steps, rather than the insoluble fraction, which is discarded. This is in contrast with the process outlined in FIG. 1B, where the *botulinum* toxin complex is contained in the insoluble fraction from pre-chromatography steps that do not involve acid precipitation, such as e.g., as a centrifugation pellet, obtained from pre-chromatography centrifugation, and the supernatant is discarded.

Moreover, and again in contrast with the process outlined in FIG. 1B, the pre-chromatography steps in some embodiments of the invention do not require a tangential flow filtration step of a filtrate obtained from fermentation culture. That is, the sample used for chromatography purification in some embodiments of the invention is not obtained by subjecting a soluble fraction of the fermentation culture to tangential flow filtration. Rather, in certain embodiments, the present invention uses insoluble material (such as an acid precipitate), eliminating any step where a fermentation culture filtrate is subjected to tangential flow filtration in an attempt to concentrate soluble *botulinum* toxin complexes.

Thus, in preferred embodiments, the pre-chromatography steps of the invention eliminate the need for any such step, by instead using acid to precipitate the desired toxin complexes with other insoluble material (cell debris).

Chromatography Purification Steps

FIG. 1A also illustrates chromatographic purification steps according to certain embodiments of the instant invention. According to one embodiment of the invention, chromatographic methods for purifying a non-complexed *botulinum* toxin comprise passing a sample comprising *botulinum* toxin through a plurality of chromatography columns to obtain a highly purified, highly potent, non-complexed form of the neurotoxin.

In certain embodiments, a complexed *botulinum* toxin is separated from other cellular components using a hydrophobic interaction chromatography column (see e.g., FIG. 1A). This column captures the *botulinum* toxin in complexed form, while allowing impurities to flow through the column. The column used may be any hydrophobic interaction column known in the art suitable for such purpose, such as a BUTYL SEPHAROSE® FAST FLOW column or a PHENYL SEPHAROSE® HIGH PERFORMANCE (HP) column, commercially available from GE Healthcare Life Sciences. In some embodiments, the method further comprises conditioning the sample for hydrophobic interaction chromatography before loading onto the column. For example, for use in the PHENYL SEPHAROSE® HP column, the sample may be combined with a 0.5M ammonium sulfate solution at pH 6, and 50 mM phosphate before loading. Other columns, buffers and pH conditions that may be used include columns such as PHENYL SEPHAROSE® FAST FLOW high substitution, PHENYL SEPHAROSE® FAST FLOW low substitution, BUTYL SEPHAROSE®, and OCTYL SEPHAROSE® hydrophobic interaction chromatography columns; buffers such as acetate, citrate, MES, histidine, piperazine, and malonate, each in the pH range of about 4.0 to about 7.0, more preferably, about 4.5 to about 6.5, and even more preferably, about 5.5. Other buffer and pH conditions may be determined to optimize yield from a particular column used, as known in the art, based on the teachings provided herein. Without wishing to be bound by theory, it is believed that separation involves binding of the toxin complex to resin at a pH below 7, to avoid dissociation at this step, while allowing many cell-derived impurities to flow through, such as, e.g., smaller proteins, nucleic acids, and the like.

For eluting the captured (bound) toxin from the hydrophobic interaction column, a suitable buffer can be used, as known in the art. In some particularly preferred embodiments, a descending gradient of ammonium sulfate is used. The concentration range of the descending gradient may be from about 0.6 M to about 0.0 M, about 0.5 M to about 0.0 M, or about 0.4 M to about 0.0 M. Other eluting buffers that may be used include, for example descending gradients of sodium sulfate ($Na_2SO_4$); sodium chloride (NaCl); potassium chloride (KCl); ammonium acetate ($NH_4OAc$); and the like. Fraction(s) containing a product peak can be identified, as known in the art. The peak fraction is typically found, e.g., when using ammonium sulfate, in a concentration range of about 0.4 M to about 0.0 M; more preferably about 0.3 M to about 0.0 M; and most preferably about 0.25 M to about 0.0 M ammonium sulfate, while the pH is kept at about 6 to maintain the complex. That is, the fraction(s) containing the eluted *botulinum* toxin complex can be identified and used in subsequent purification steps.

In preferred embodiments, the *botulinum* toxin complex obtained is caused to dissociate to give a non-complexed form. In certain preferred embodiments, the dissociation step is performed after the hydrophobic interaction chromatography step and/or before subsequent chromatography steps (e.g., see FIG. 1A). Accordingly, in some preferred embodiments, the instant invention encompasses methods and systems where the chromatographic target molecule differs from one chromatographic step to another. That is, in an initial chromatographic step, the target comprises a *botulinum* toxin complex, whereas in subsequent chromatographic steps, the target comprises the free *botulinum* toxin, dissociated from non-toxin proteins such as hemagglutinin and non-hemagglutinin proteins. In contrast, the process outlined in FIG. 1B involves chromatography steps that are all designed to purify *botulinum* toxin complexes.

Dissociation of the *botulinum* toxin complex to produce the non-complexed *botulinum* toxin protein may be achieved in a number of ways, e.g., as known in the art and/or described herein. For example, dissociation may be achieved by raising the pH to about 7.0; or, in embodiments in which animal protein free purification is not necessary, treating the complex with red blood cells at a pH of about 7.3.

In a preferred embodiment and to provide animal free toxin, the complex is subjected to a separation process based on adjustment pH of the complex in a suitable buffer Suitable buffers include, but are not limited to, cationic buffers, preferably cationic buffers that will not interact or will not substantially interact with the anion exchange column. Suitable cationic buffers include, e.g., Tris, bis-Tris, triethanolamine, N-methyl diethanolamine. A pH of between about 7 to about 8.4; more preferably between about 7.4 to about 8.2; and most preferably a pH of about 7.8 is typically suitable for dissociating the complex to release the non-complexed *botulinum* toxin. In some particularly preferred embodiments, for example, the pH of the eluent of the hydrophobic interaction column is raised to about 7.5, about 7.8, or preferably to about 8.0. For example, in some embodiments, the eluent may be diluted into a Tris buffer having a pH of about 7.8 to cause the complex to dissociate into individual components, including the about 150 kD non-complexed *botulinum* toxin protein. The resulting mixture comprising dissociated components can then be subjected to one or more additional chromatography purification steps, such as ion exchange chromatography steps designed to capture and further purify the non-complexed toxin.

In certain embodiments according to the invention, the non-complexed *botulinum* toxin may be purified using one or more ion exchange chromatography steps, (e.g., see FIG. 1A). Ion exchange chromatography achieves fractionation based on electrostatic charge. The extent to which a given protein binds to the column matrix is a function of the protein's net charge, based on its individual amino acid composition and the charge of the column matrix. Cationic ion exchange columns have net positive charged matrix whereas anionic ion exchange columns have a net negative charged matrix. Bound proteins can be selectively eluted from the column using a solvent (the eluant) containing a charged substance, such as salt ions, which competes with the charged matrix support for binding to the charged proteins. Bound proteins can be thus fractionated on the basis of the strength of their charge. Alternatively, proteins may be eluted by adjusted the pH which may alter the net charge of the protein thereby altering its affinity to the charged matrix.

According to some preferred embodiments of the invention, the mixture comprising non-complexed *botulinum* toxin is loaded onto an anion exchange column (e.g., see FIG. 1A). Notably, this column captures the *botulinum* toxin in non-complexed form, such that the toxin protein and dissociated non-toxin proteins can be eluted in separate fractions. The column used may be any anion exchange chromatography column containing resins known in the art suitable for separating charged proteins, non-limiting examples of which include SEPHAROSE® HP, SEPHAROSE® FAST FLOW, or Q XL SEPHAROSE®, commercially available from GE Healthcare Life Sciences. In some particularly preferred embodiments, a Q XL SEPHAROSE® column is used. In some embodiments, the method further comprises conditioning the mixture comprising the non-complexed *botulinum* toxin for anion exchange chromatography before loading onto the column. For example, buffer and pH conditions may be determined to optimize yield from the particular column used, as known in the art, based on the teachings provided herein. For loading and use in the column, e.g., suitable buffers include, but are not limited to, cationic buffers, preferably cationic buffers that will not interact or will not substantially interact with the anion exchange column. Suitable cationic buffers include, e.g., Tris, bis-Tris, triethanolamine, N-methyl diethanolamine. For loading and equibrilating the column, a pH of between about 7.2 to about 8.6; more preferably between about 7.4 to about 8.2; and most preferably, a pH of about 7.8 may be used.

For eluting the captured (bound) toxin and other dissociated components from the anion exchange column, a suitable buffer can be used, as known in the art. Examples of suitable buffers include, for example, sodium chloride (NaCl); and potassium chloride (KCl). In some particularly preferred embodiments, an ascending gradient of sodium chloride is used. For example, a sodium chloride buffer having a concentration range from about 0.0 M to about 0.4 M NaCl, more preferably from about 0.0 M to about 0.5 M NaCl, and even more preferably about 0.0 M to about 0.6 M NaCl may be used. Impurities separated in different fractions may include, e.g., one or more non-toxin proteins of the dissociated complex, such as, the non-toxin hemagglutinin and/or non-toxin non-hemagglutinin proteins. Fraction(s) containing a product peak can be identified, as known in the art. The peak may occur, for example, at about 8 mSem to about 22 mSem at a pH between about 7.4 to about 8.4, and preferably at about 7.8, corresponding to about 0.08 M to about 0.18 M NaCl. Conversely, other impurities may elute at about 30 to about 45 mSem, corresponding to about 0.25 M to about 0.35 M NaCl.

The fraction(s) containing the eluted non-complexed *botulinum* toxin can be identified to provide an eluent comprising a non-complexed *botulinum* toxin. The peak may be identified by methods as known in the art, e.g., using HPLC, western blot analysis, ELISA, non-reduced SDS-PAGE, and the like. SDS-PAGE under non-reducing conditions, for example, can identify the about 150 kDa toxin band, whereas other impurities will appear at bands corresponding to smaller molecules. This eluent comprising a non-complexed form may then be subjected to further chromatographic purification steps.

In one particularly preferred embodiment, toxin purity is assessed by SDS-PAGE. As the skilled artisan will appreciate, SDS-PAGE analysis can be conducted in the absence or presence of agents that cleave disulfide bonds present in the protein (i.e., non-reducing or reducing conditions, respectively). For example, with respect to *botulinum* toxin type A, the mature and active form of the *botulinum* toxin type A protein molecule is comprised of two polypeptide chains of 100 kD and 50 kD, respectively, which are held together by non-covalent interactions as well as a disulfide bond. When *botulinum* toxin type A produced by the inventive process is assayed using non-reducing conditions, the *botulinum* toxin type A protein molecules migrate as a single protein band of approximately 150 kD and the measured purity is typically greater than 98%. When the *botulinum* toxin type A protein amount loaded per gel lane is held to be within the dynamic range of the densitometer, then there are few, if any, detectable impurity bands resulting in a measured purity of 100%. When the type A *botulinum* toxin is overloaded such that the main toxin band is above the dynamic range of the densitometer, then some minor impurity bands may be detectable (as much as 1-2%).

However, when the SDS-PAGE analysis of *botulinum* toxin type A is conducted under reducing conditions, then the disulfide bond of the *botulinum* toxin is cleaved and the *botulinum* toxin type A protein migrates as two components having molecular weights of 100 kD and 50 kD, respectively. When the *botulinum* toxin type A protein is loaded such that the main species are above the dynamic range of the densitometer and the SDS-page is run under reducing conditions then minor impurity species can be more easily detected. For instance, under these conditions there may be as much as 5% of the 150 kD species present due to incomplete proteolytic processing during the fermentation and recovery process. Under these conditions the inventive process yields a toxin product (comprised of the active, cleaved 100 kD and 50 kD polypeptide chains) that is typically greater than 90% of total protein and more likely greater than 95% of total protein. Thus, the reported measured purity of the toxin depends on the details of the SDS-PAGE method employed, as described herein. Furthermore, while the foregoing example concerns *botulinum* toxin type A, the skilled artisan will appreciate that the SDS-PAGE analysis described herein can be readily adapted to assess the purity of other serotypes of *botulinum* toxin.

In certain embodiments, the eluent from the anionic chromatography column comprising non-complexed *botulinum* toxin is loaded onto a cation exchange chromatography column (see, e.g. FIG. 1A). Notably, this column also captures the *botulinum* toxin in non-complexed form, such that the toxin protein and dissociated non-toxin proteins can be eluted in separate fractions. The column used may be any cation exchange chromatography column containing resins known in the art suitable for separating proteins, non-limiting examples of which include an SP SEPHAROSE® column, including SP SEPHAROSE® HP or SP FAST FLOW, MONO S column or a SOURCE-S column, such as a SOURCE-30S column, or preferably a SOURCE-15S column, both commercially available from GE Healthcare Life Sciences. In some embodiments, the method further comprises conditioning the eluent from the anionic exchange columns comprising non-complexed *botulinum* toxin for cation exchange chromatography before loading onto the column. In some preferred embodiments, the pH is adjusted so that the pH of the eluent being loaded on the column allows for efficient binding of the free toxin to the column. For example, the pH can be maintained within a range of from about 4 to about 8, preferably from about 5 to about 7.5, more preferably from about 6 to about 7, and most preferably at about 7. Further, in some embodiments, the eluent from the anionic column can be treated to reduce conductivity before loading onto the cation exchange column, e.g., using a sodium phosphate buffer, a non-limiting example of which is a sodium phosphate buffer of about 20 mM $NaH_2PO_4$. For example, the eluent from the anionic column may contain as much as about 0.15 M NaCl, so that diluting in an about 20 mM $NaH_2PO_4$ buffer reduces conductivity. In some specific embodiments, conductivity is reduced from about 12 mSem to about 3.3 mSem. Dilution in buffer, dialysis or other methods known in the art also may be used to reduce the conductivity.

For loading and use in the column, e.g., suitable buffers include, but are not limited to, anionic buffers, preferably anionic buffers that will not interact or will not substantially interact with the cationic exchange column. Suitable anionic buffers include, e.g., as MES, HEPES, and the like, and preferably sodium phosphate buffer. For loading and equilibrating the column, a pH of between about 4 to about 8; preferably between about 5 to about 7.5; more preferably from about 6 to about 7; and most preferably a pH of about 6.8 to about 7 may be used.

For eluting the captured (bound) toxin from the cation exchange column separately from other dissociated non-toxin proteins and other impurities, a suitable buffer can be used, as known in the art. In some particularly preferred embodiments, an ascending gradient of sodium chloride is used. A suitable concentration range for the sodium chloride gradient may be from about 0.0 M to about 1 M NaCl. Other salts that may be used include, e.g., potassium chloride, that may be used at a concentration gradient of about 0.0 M to about 0.5 M KCl. Fraction(s) containing a product peak can be identified, as known in the art. The peak may occur, for example from about 18 to about 25 mSem, corresponding to about 0.3 M to about 0.4 M NaCl, at a pH of about 6.7. That is, the fraction(s) containing the eluted non-complexed *botulinum* toxin can be identified to provide an eluent from the cationic column comprising non-complexed *botulinum* toxin. In particularly preferred embodiments, the eluent from the cationic column represents a non-complexed *botulinum* toxin of high purity, in high yield and having high activity. In contrast, the process outlined in FIG. 1B provides a 900 kD *botulinum* toxin type A complex in the final eluent.

Purified Non-Complexed *Botulinum* Toxin Product

The methods and systems described herein are useful to provide a non-complexed *botulinum* toxin of high purity, in high yield, and having high activity. See Example 1 below. The product is also readily stabilized and conveniently used for the preparation of safe pharmaceutical compositions.

In some preferred embodiments, the purified non-complexed *botulinum* toxin is at least about 80% pure, preferably at least about 90% pure, more preferably at least about 95% pure, even more preferably at least about 98% pure, and most preferably at least about 99% pure, or even about 100% pure. "Purified non-complexed *botulinum* toxin" refers to a free *botulinum* toxin protein molecule that is isolated, or substantially isolated, from other proteins and impurities, which can otherwise accompany the non-complexed *botulinum* toxin as it is obtained from a culture or fermentation process. A purified non-complexed *botulinum* toxin that is, for example, "80% pure" refers to an isolated or substantially isolated non-complexed *botulinum* toxin protein wherein the toxin protein comprises 80% of total protein present as determined by or other suitable analytical methodology, non-limiting examples of which include SDS-PAGE, CE, and HPLC. For example, in some preferred embodiments, the cationic column eluent comprising the non-complexed *botulinum* toxin is at least about 99% pure, and contains less than about 1% of host cell proteins that are not the approximately 150 kD *botulinum* toxin originally present.

In some preferred embodiments, the purified non-complexed *botulinum* toxin has an activity of at least about 150 $LD_{50}$ units/ng, preferably at least about 180 $LD_{50}$ units/ng, more preferably at least about 200 $LD_{50}$ units/ng, even more preferably at least about 210 $LD_{50}$ units/ng, and most preferably at least about 220 $LD_{50}$ units/ng. One unit of *botulinum* toxin is defined as the $LD_{50}$ upon intraperitoneal injection into female Swiss Webster mice weighing about 18-20 grams each. In other words, one unit of *botulinum* toxin is the amount of *botulinum* toxin that kills 50% of a group of female Swiss Webster mice. "Activity" is used interchangeably herein with related expressions "biological activity", "potency" and "toxicity" to describe the action of a *botulinum* toxin.

In preferred embodiments, the non-complexed *botulinum* toxins obtainable by processes and systems described herein demonstrate biological activity. That is, in preferred embodiments, the biological activity or toxicity of the product is not lost upon purification in accordance with preferred embodiments of the present invention, even though non-toxin proteins natively associated with the toxin protein are removed during purification. In even more preferred embodiments, the potency obtained using a given set of processes and parameters within the scope of the invention is consistent and/or reproducible. For example, the potency measurement can be made with less than about 40% variability, preferably less than about 35% variability, more preferably less than about 30% variability, even more preferably less than about 25% variability, and most preferably less than about 20% variability.

In some preferred embodiments, the purification process provides the non-complexed *botulinum* toxin in high yield. For example, the yield obtained from 30 L of a fermentation culture may be at least about 30 mg, preferably at least about 40 mg, more preferably at least about 70 mg, even more preferably at least about 80 mg, and most preferably at least about 90 mg, corresponding to a yield of at least about 1 mg/L, preferably at least about 1.3 mg/L, more preferably at least about 2.3 mg/L, even more preferably at least about 2.7 mg/L, and most preferably at least about 3 mg/L, respectively. In even more preferred embodiments, the yield obtained using a given set of processes and parameters within the scope of the invention is reproducible. For example, yield can be measured with less than about 40% variability, preferably less than about 35% variability, more preferably less than about 30% variability, even more preferably less than about 25% variability, and most preferably less than about 20% variability.

In some particularly preferred embodiments, the purified non-complexed *botulinum* toxin is stable during purification using the processes and systems described herein. It has been believed that removal of associated non-toxin proteins from a *botulinum* toxin complex, such as *botulinum* toxin type A complex, results in a markedly unstable *botulinum* toxin product. The instant invention, however, provides methods and systems that can stably isolate free *botulinum* toxin, without associated non-toxin proteins conventionally believed necessary during the purification process to maintain stability, as discussed above.

In some preferred embodiments, methods and systems described herein provide a non-complexed *botulinum* toxin that requires very few post-chromatography steps, e.g., in terms of maintaining stability during storage, and in terms of applicability to pharmaceutical uses. For example, as known in the art, ammonium sulfate may be added to the free *botulinum* toxin to prepare an ammonium sulfate suspension for storage. The composition comprising free *botulinum* toxin and ammonium sulfate may be readily stored in a refrigerator and later can be readily retrieved for use in pharmaceutical applications. Indeed, the stability, high yield and purity, and high and consistent potency of the toxin obtainable by methods described herein facilitate pharmaceutical use of the purified product, as described in more detail below.

Uses of Purified Non-Complexed *Botulinum* Toxin

The non-complexed *botulinum* toxin purified according to this invention can be used in the preparation of pharmaceutical compositions comprising the toxin as an active ingredient for administration to any subject who would receive a benefit from such pharmaceutical compositions. In preferred embodiments, the subjects to be treated are mammals, preferably humans. "Pharmaceutical composition" as used herein refers to a formulation in which an active ingredient can be a *botulinum* toxin. The formulation will contain at least one additional ingredient and be suitable for diagnostic, therapeutic, and/or or cosmetic administration to a subject, such as a human patient. The pharmaceutical composition can be liquid or solid; and may be a single or multi-component system, for example a lyophilized composition reconstituted with a diluent such as saline.

Another aspect of the invention provides for administration of a purified *botulinum* toxin molecule to a patient. "Administration" as used herein refers to providing a pharmaceutical composition to a subject or patient. The pharmaceutical composition may be administered by, any method known in the art, including e.g., intramuscular (i.m.), intradermal, intranasal, or subcutaneous administration, intrathecal administration, intracranial, intraperitoneal (i.p.) administration, or topical (transdermal) and implantation (e.g., of a slow-release device) routes of administration. In certain preferred embodiments, the purified non-complexed *botulinum* toxin is administered topically or by injection in compositions as described in U.S. patent application Ser. Nos. 09/910,432; 10/793,138; 11/072,026; 11/073,307, 11/824,393, and 12/154,982, which are hereby incorporated by reference in their entireties.

In certain embodiments, compositions comprising non-complexed *botulinum* toxin in an ammonium sulfate suspension can be readily compounded into a pharmaceutical composition. For example, an ammonium sulfate suspension comprising non-complexed *botulinum* toxin protein can be centrifuged to recover the protein and the protein can be re-solubilized, diluted, and compounded with one or more pharmaceutically acceptable excipients. In certain embodiments, the pharmaceutical composition may comprise a non-complexed *botulinum* toxin as an active pharmaceutical ingredient, and may further comprise one or more buffers, carriers, stabilizers, preservatives and/or bulking agents. The pharmaceutical compositions may be lyophilized to powder for storage, and re-constituted for further use. Accordingly, processes and systems described herein can provide a *botulinum* toxin in a form particularly suited to pharmaceutical applications terms of ease of preparation.

The pharmaceutical composition may find use in therapeutic, diagnostic, research and/or cosmetic applications. For example, as discussed above, *botulinum* toxin type A is clinically used to treat neuromuscular disorders characterized by skeletal muscle hyperactivity, such as essential blepharospasm, strabismus, cervical dystonia, and glabellar line (facial) wrinkles. Moreover, in certain applications, non-complexed (about 150 kD) *botulinum* toxin is the preferred form for treating humans. See, e.g., Kohl A., et al., Comparison of the effect of *botulinum* toxin A (Botox®) with the highly-purified neurotoxin (NT 201) in the extensor digitorum *brevis* muscle test, Mov Disord 2000; 15(Suppl 3):165. Accordingly, certain *botulinum* toxin pharmaceutical compositions are preferably prepared using non-complexed *botulinum* toxin, as opposed to a *botulinum* toxin complex.

EXAMPLES

Example 1

Comparison of Inventive Process with a Modified Schantz Process

Purifications of non-complexed *botulinum* toxin type A using processes within the scope of the instant invention ('inventive process") were directly compared to purifications based on the traditional Schantz approach, further modified by the addition of chromatographic steps to provide the non-complexed form (Modified Schantz process"). Briefly, *Clostridium botulinum* bacteria were cultured and allowed to grow until fermentation was complete (usually about 72 to about 120 hours from inoculation to harvest). A volume of 30 L of the fermentation culture then was used in each of the following purification procedures.

The modified Schantz process used involved typical acidification of the fermentation culture to precipitate the toxin, followed by ultramicrofiltration (UF) and diafiltration (DF) to concentrate the raw toxin. DNase and RNase were added to the harvested toxin to digest (hydrolyze) nucleic acids, which were then removed by an additional UF step, using tangential flow filtration (300 kD UF). The toxin was next extracted with phosphate buffer, followed by three sequential precipitation steps: cold ethanol precipitation; hydrochloric acid precipitation, and ammonium sulfate precipitation, where the supernatants each time were normally discarded. This procedure provided a 900 kD *botulinum* toxin type A complex, which was then subjected to additional chromatography steps to provide the free toxin. Specifically, the toxin complex was resolubilized and subjected to negative batch adsorption onto a DEAE resin. The eluent was then run on a gravity flow anion exchange column (DEAE SEPHAROSE®), followed by a gravity flow cation exchange column (CM-SEPHAROSE®). Yield was determined, the length of time the process took was recorded (not counting the fermentation period), and the purified non-complexed *botulinum* toxin type A was measured for purity by SDS-PAGE analysis and assayed for potency, e.g., by techniques known to those skilled in the art. The entire modified Schantz process was repeated for three different lots, lot numbers 1, 2 and 3, and the results recorded in Table 1 below.

The inventive process was used with three different lots, lot numbers 4, 5 and 6, in accordance with systems and methods described herein. Briefly, the fermentation culture was subjected to acid precipitation using 3M sulfuric acid to reduce pH to 3.5, at a temperature below 25° C. The acid precipitate was then subjected to 0.1 μm tangential flow filtration to concentrate cell mass. The pH then was adjusted to 6 and nucleases added to reduce host cell nucleic acid content, followed by clarification by centrifugation to remove cell debris and dead end filtration at 0.2 μm with added ammonium sulfate. The filtrate was then directly loaded onto the hydrophobic interaction column, PHENYL SEPHAROSE® HP (GE Life Sciences), eluted with a descending gradient of ammonium sulfate, and the product peak isolated. The eluent was then diluted into Tris buffer pH 7.8 to dissociate the toxin complex, which then was loaded onto the anion exchange column Q XL SEPHAROSE® (GE Lifesciences), eluted with an ascending gradient of sodium chloride, and again the product peak collected. This eluent was then diluted in a sodium phosphate buffer (to reduce conductivity) and loaded onto either the anion exchange column, Q XL SEPHAROSE® (for lots #4 and 5), or the cation exchange column, SOURCE-S (GE Life Sciences) (for lot #6), again eluted with an ascending gradient of sodium chloride, and a final product peak collected and stored. This process yielded non-complexed *botulinum* toxin type A. Yield was determined, the length of process time recorded (not counting the fermentation period), and the toxin measured for purity by SDS-PAGE analysis and assayed for potency, e.g., by techniques known to those skilled in the art. Results also recorded Table 1 below.

TABLE 1

| | Modified Schantz Process | | | Inventive Process | | |
|---|---|---|---|---|---|---|
| Lot # | 1 | 2 | 3 | 4 | 5 | 6 |
| Process Time | 10 days | | | 4 days | | |
| % Purity | 99 | n/a | 97 | 98.6 | 95.3 | 100 |
| Yield (30 L scale) | 11 mg | 0 mg | 4 mg | 43 mg | 99 mg | 89 mg |
| Potency ($LD_{50}$ Units/ng) | 255 | n/a | 173 | 259 | 252 | 250 |

As Table 1 indicates, there was a lot failure with respect to lot #2 in the modified Schantz process. The total lot failed giving zero yield. There was also a partial lot failure with respect to lot #3. There the failure occurred at the hydrochloric acid precipitation step, but some product was rescued from the normally discarded supernatant. The rescued product was reprocessed with a deviation step, accounting for the observed reduced yield compared with lot #1 (4 mg compared with 11 mg) and the observed reduced potency compared with lot #1 (173 $LD_{50}$ units/ng compared with 255 $LD_{50}$ units/ng).

With respect to the lots used with the inventive process, lot #4 showed a reduced yield, compared to lot #5 for example (43 mg compared with 99 mg) due to a chromatography system failure, involving high salt wash of a column. With the failure, there was premature elution of a portion of the toxin, resulting in the observed reduced yield, but also an observed higher purity (98.6% purity compared with 95.3% purity).

Lot #6 represents the results of a highly preferred embodiment of the instant inventive processes and systems, where a cation exchange column was used in the third chromatography step. As Table 1 indicates, this embodiment resulted in improved purity compared with lot #5 for example (100% purity compared with 95.3% purity), while high yield (89 mg compared with 99 mg) and high potency (250 $LD_{50}$ units/ng compared with 252 $LD_{50}$ units/ng) were maintained.

As Table 1 also indicates, the total length of the purification can be shortened in preferred embodiments of the instant invention. For example, lot #6 was purified within only 4 days, compared to the 10 days it took to purify non-complexed *botulinum* toxin using the modified Schantz method that involved three additional chromatography steps after the conventional Schantz method.

The results indicate that the processes and systems taught herein can be used to prepare high yields of a non-complexed *botulinum* toxin, at high potency and purity, and suggests that methods and systems described herein can find use in large-scale efficient purification of a non-complexed *botulinum* toxin suitable for use, e.g., as an active ingredient in pharmaceutical compositions.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for purifying a non-complexed *botulinum* toxin type A (*botulinum* toxin A), the method comprising:
   (a) providing a mixture comprising a crude non-complexed *botulinum* toxin A, in which said crude non-complexed *botulinum* toxin A is dissociated from native non-toxin proteins; wherein said mixture is obtained by:
      (i) subjecting a fermentation culture comprising *botulinum* toxin A to acid precipitation to produce an insoluble acid precipitate;
      (ii) concentrating the acid precipitate from step (i) to produce a concentrated sample;
      (iii) subjecting the sample to nuclease digestion under conditions which reduce host cell nucleic acid content and which maintain a complex of *botulinum* toxin A and non-toxin proteins;
      (iv) removing cell debris from the sample of step (iii) to produce a clarified sample;
      (v) loading a hydrophobic interaction column with the clarified sample from step (iv) under conditions to permit capture of the *botulinum* toxin A complex by the hydrophobic interaction column and impurities to flow through the column;
      (vi) eluting the *botulinum* toxin A complex from the hydrophobic interaction column of step (vi); and
      (vii) dissociating the *botulinum* toxin A complex obtained from step (vi) under conditions which disrupt the complex and produce a mixture comprising crude non-complexed *botulinum* toxin A dissociated from the native non-toxin proteins;
   (b) loading the mixture containing the crude non-complexed *botulinum* toxin A dissociated from native non-toxin proteins from step (a) on an anion exchange column under conditions permitting capture of the non-complexed *botulinum* toxin A by the anion exchange column;
   (c) eluting the non-complexed *botulinum* toxin A from the anion exchange column of step (b) to give an eluent comprising the non-complexed *botulinum* toxin A;
   (d) loading a cation exchange column with the eluent from the anion exchange column of step (c) under conditions permitting capture of the non-complexed *botulinum* toxin A by the cation exchange column; and
   (e) eluting purified non-complexed *botulinum* toxin A from the cation exchange column of step (d).

2. The method according to claim 1, wherein, in step (i), the fermentation culture comprising *botulinum* toxin A is acid precipitated with sulfuric acid.

3. The method according to claim 2, wherein the concentrated sample of step (ii) is obtained by performing tangential flow filtration on the acid precipitate to concentrate the precipitate.

4. The method according to claim 1, wherein the sample of step (iii) is subjected to nuclease digestion at a pH of 5 to 7.

5. The method according to claim 4, wherein the nuclease is derived from a non-animal source.

6. The method according to claim 5, wherein, in step (iv), the cell debris is removed by centrifugation and/or filtration to produce the clarified sample.

7. The method according to claim 6, wherein the clarified sample of step (iv) is combined with a buffer comprising ammonium sulfate prior to loading the hydrophobic interaction column in step (v).

8. The method according to claim 7, wherein the clarified sample of step (iv) is combined with a buffer comprising ammonium sulfate and phosphate at pH 6 prior to loading the hydrophobic interaction column in step (v).

9. The method according to claim 8, wherein, in step (vii), the *botulinum* toxin A complex is dissociated in a buffer having a pH of 7.0 to 8.4 to obtain the mixture comprising the crude non-complexed *botulinum* toxin A dissociated from the native non-toxin proteins.

10. The method according to claim 9, wherein the *botulinum* toxin A complex is dissociated in Tris buffer at pH 7.8.

11. The method according to claim 10, wherein the method is substantially animal product free.

12. The method according to claim 11, wherein the hydrophobic interaction column comprises a chromatography gel matrix comprising beaded agarose, having attached thereto chemical groups selected from butyl, octyl, or phenyl groups.

13. The method according to claim 12, wherein a loading or equilibration buffer for the hydrophobic interaction column is selected from acetate, citrate, 2-(N-morpholino)ethanesulfonic acid (MES), histidine, piperazine and malonate.

14. The method according to claim 13, wherein the pH of the hydrophobic interaction column buffer is in the range of pH 4.0 to 7.0.

15. The method according to claim 14, wherein the pH of the hydrophobic interaction column buffer is in the range of pH 4.5 to 6.5.

16. The method according to claim 15, wherein the pH of the hydrophobic interaction column buffer is pH 6.

17. The method according to claim 12, wherein the bound *botulinum* toxin A complex is eluted from the hydrophobic interaction column in a descending gradient of an elution buffer selected from the group consisting of ammonium sulfate, sodium sulfate, sodium chloride, potassium chloride and ammonium acetate.

18. The method according to claim 17, wherein the elution buffer is ammonium sulfate.

19. The method according to claim 17, wherein the concentration range of the descending gradient elution buffer is from 0.6 M to 0.0 M.

20. The method according to claim 17, wherein the concentration range of the descending gradient elution buffer is from 0.5 M to 0.0 M.

21. The method according to claim 17, wherein the concentration range of the descending gradient elution buffer is from 0.4 M to 0.0 M.

22. The method according to claim 17, wherein the concentration range of the descending gradient elution buffer is from 0.25 M to 0.0 M.

23. The method according to claim 12, wherein the bound *botulinum* toxin A complex is eluted from the hydrophobic interaction column in a descending gradient of ammonium sulfate elution buffer in a concentration range of 0.4 M to 0.0 M at pH 6.

24. The method according to claim 17, wherein the anion exchange column comprises a chromatography gel matrix comprising beaded agarose having a net negative charge, and wherein the cation exchange column comprises a chromatography gel matrix comprising beaded agarose having a net positive charge; wherein said anion and cation exchange columns provide separation of proteins based on electrostatic charge.

25. The method according to claim 24, wherein the non-complexed *botulinum* toxin A is loaded onto the anion exchange column in a buffer selected from the group consisting of Tris, bis-Tris, triethanolamine, and N-methyl diethanolamine.

26. The method according to claim 25, wherein the buffer is used at a pH from 7.2 to 8.6.

27. The method according to claim 25, wherein the buffer is used at a pH from 7.4 to 8.2.

28. The method according to claim 24, wherein the non-complexed *botulinum* toxin A is loaded onto the cation exchange column in a buffer selected from the group consisting of sodium phosphate, 2-(N-morpholino)ethanesulfonic acid (MES) and HEPES.

29. The method according to claim 28, wherein the buffer is used at a pH of from 6.0 to 7.0.

30. The method according to claim 24, wherein the pH of the anion exchange column is from 7.4 to 8.2.

31. The method according to claim 30, wherein the buffer is used at a pH of from 6.8 to 7.0.

32. The method according to claim 24, wherein a concentration gradient of an elution buffer for eluting the non-complexed *botulinum* toxin A from the anion exchange column is selected from the group consisting of an ascending concentration gradient of sodium chloride and an ascending concentration gradient of potassium chloride.

33. The method according to claim 32, wherein the concentration range of the ascending gradient is from 0.0 M to 0.6 M.

34. The method according to claim 32, wherein concentration range of the ascending gradient is from 0.0 M to 0.5 M.

35. The method according to claim 32, wherein the ascending concentration gradient of sodium chloride has a concentration range of 0.0 M to 0.6 M.

36. The method according to claim 32, wherein the anion exchange column is eluted at a pH from 7.4 to 8.4.

37. The method according to claim 24, wherein a gradient for eluting the non-complexed *botulinum* toxin A from the cation exchange column is selected from the group consisting of an ascending concentration gradient of sodium chloride and an ascending concentration gradient of potassium chloride.

38. The method according to claim 37, wherein the concentration range of the ascending gradient of sodium chloride is from 0.0 M to 1 M.

39. The method according to claim 37, wherein concentration range of the ascending gradient of potassium chloride is from 0.0 M to 0.5 M.

40. The method according to claim 37, wherein the cation exchange column is eluted at a pH from 6.0 to 7.0.

41. The method according to claim 40, wherein the pH of the cation exchange column is pH 7.

42. The method according to claim 15, wherein the pH of the hydrophobic interaction column buffer is in the range of pH 5.5 to 6.5.

43. The method according to claim 18, wherein the bound *botulinum* toxin A complex is eluted from the hydrophobic interaction column in an ammonium sulfate buffer in a descending concentration gradient of from 0.6 M. to 0.0 M.

44. The method according to claim 18, wherein the bound *botulinum* toxin A complex is eluted from the hydrophobic interaction column in an ammonium sulfate buffer in a descending concentration gradient of from 0.5 M to 0.0 M.

45. The method according to claim 18, wherein the bound *botulinum* toxin A complex is eluted from the hydrophobic interaction column in an ammonium sulfate buffer in a descending concentration gradient from 0.4 M. to 0.0 M.

46. The method according to any one of claims 43 to 45, wherein the bound *botulinum* toxin A complex is eluted from the hydrophobic interaction column at a pH of 6.0.

47. The method according to claim 26, wherein the buffer is used at a pH of pH 7.0 to 8.4.

48. The method according to claim 28, wherein the pH of the cation exchange column buffer is in the range of pH 4.0 to 8.0.

49. The method according to claim 48, wherein the pH of the cation exchange column buffer is in the range of pH 5.0 to 7.5.

50. The method according to claim 1 or claim 25, wherein the non-complexed *botulinum* toxin A is eluted from the anion exchange column in a buffer selected from sodium chloride or potassium chloride in an ascending concentration gradient of 0.0 M to 0.6 M.

51. The method according to claim 50, wherein the non-complexed *botulinum* toxin A is eluted from the anion exchange column in an ascending concentration gradient of sodium chloride in a concentration range of 0.0 M to 0.4 M.

52. The method according to claim 50, wherein the non-complexed *botulinum* toxin A is eluted from the anion exchange column in an ascending concentration gradient of sodium chloride in a concentration range of 0.0 M to 0.5 M.

53. The method according to claim 50, wherein the non-complexed *botulinum* toxin A is eluted from the anion exchange column in an ascending concentration gradient of sodium chloride in a concentration range of 0.0 M to 0.6 M.

54. The method according to claim 50, wherein the non-complexed *botulinum* toxin A is eluted from the anion exchange column at a pH of 7.4 to 8.4.

55. The method according claim 1 or claim 28, wherein the non-complexed *botulinum* toxin A is eluted from the cation exchange column in an ascending concentration gradient of sodium chloride in a concentration range of from 0.0 M to 1.0 M.

56. The method according to claim 1 or claim 28, wherein the non-complexed *botulinum* toxin A is eluted from the cation exchange column in an ascending concentration gradient of potassium chloride in a concentration range of from 0.0 M to 0.5 M.

57. The method according to claim 55, wherein the non-complexed *botulinum* toxin A is eluted from the cation exchange column at a pH of 6 to 7.

58. The method according to claim 1, wherein the purified non-complexed *botulinum* toxin A is at least 95% pure and/or has an activity of at least 200 $LD_{50}$ units/ng.

59. The method according to any one of claim 1, 11 or 58, wherein said method produces a yield of at least about 1 mg to at least about 3 mg of purified non-complexed *botulinum* toxin A per liter (L) of fermentation culture.

60. The method according to claim 59, wherein the method produces a yield of about 1 to about 2 mg per liter (L) of fermentation culture.

61. The method according to claim 59, wherein the method produces a yield of at least about 3 mg of purified non-complexed *botulinum* toxin A per liter (L) of fermentation culture.

62. The method according to claim 59, wherein the method produces a yield of at least about 2 mg of purified non-complexed *botulinum* toxin A per liter (L) of fermentation culture.

63. The method according to claim 59, wherein the method produces a yield of at least about 1 mg of purified non-complexed *botulinum* toxin A per liter (L) of fermentation culture.

64. The method according to claim 56, wherein the non-complexed *botulinum* toxin A is eluted from the cation exchange column at a pH of 6 to 7.

65. The method according to claim 59, wherein said method produces a pure non-complexed *botulinum* toxin A of 150 kD.

66. The method according to claim 3, wherein the sample of step (iii) is subjected to nuclease digestion at a pH of 5 to 7.

67. The method according to claim 1, wherein the hydrophobic interaction column comprises a chromatography gel matrix comprising beaded agarose, having attached thereto chemical groups selected from butyl, octyl, or phenyl groups.

* * * * *